United States Patent [19]

Kano et al.

[11] Patent Number: 5,631,138
[45] Date of Patent: May 20, 1997

[54] METHOD FOR THE MEASUREMENT OF SERUM BILE ACIDS BY ELISA AND METHOD FOR THE DIAGNOSIS OF LIVER DISEASE

[75] Inventors: Motonari Kano; Masaru Matsumoto, both of Tokyo, Japan

[73] Assignee: Yuugengaisha B.S.R., Tokyo, Japan

[21] Appl. No.: 381,497

[22] Filed: Jan. 31, 1995

[30] Foreign Application Priority Data

Nov. 24, 1994 [JP] Japan .................................. 6-290104

[51] Int. Cl.$^6$ .................................................. G01N 33/53
[52] U.S. Cl. .................. 435/7.92; 435/7.93; 435/7.94; 435/7.95; 435/961; 435/973; 436/518; 436/531; 436/543; 436/544; 436/811; 436/822
[58] Field of Search ............... 424/175.1; 435/7.92–7.95, 435/28, 174, 188, 961, 973; 436/518, 530, 543, 531, 544, 547, 64, 811, 817, 822; 530/389.1, 389.8, 807, 816

[56] References Cited

U.S. PATENT DOCUMENTS

| | | | |
|---|---|---|---|
| 4,256,724 | 3/1981 | Rutner et al. | 424/1 |
| 4,410,634 | 10/1983 | Cooper et al. | 436/500 |
| 4,623,485 | 11/1986 | Kono et al. | 540/92 |
| 5,141,865 | 8/1992 | Croze et al. | 530/388.9 |

FOREIGN PATENT DOCUMENTS

WO90/11526  10/1990  European Pat. Off. .
2020014  of 0000  United Kingdom .

OTHER PUBLICATIONS

Beckett et al, "Investigations Into the Choice of Immunogen, Ligand, Antiserum, and Assay Conditions for the Radioimmunoassay of Conjugated Cholic Acid", Clinica Chemica Acta 88(1978)257–266.

Demers et al., "RIA of Bile Acids in Serum," Clin. Chem. 22(1976):602–606.
Maëntausta et al, "RIA of Conjugated Cholic Acid, Chenodeoxycholic Acid, and Deoxycholic Acid from Human Serum . . . " Clin. Chem. 25(1979):264–268.
Ross, "Radioimmunoassay of Serum Bile Acids," Methods in Enzymology 84(1982):321–349.
Chemical Abstract 91(19):153824 "Enzyme–labeled Immunoassay for a Bile Acid in Serum" (1979).
Chemical Abstract 90:164295 "Enzyme–linked Immunoassay of Ursodeoxycholic Acid in Serum" (1979).

(List continued on next page.)

*Primary Examiner*—Carol A. Spiegel
*Attorney, Agent, or Firm*—Cushman Darby & Cushman IP Group of Pillsbury Madison & Sutro LLP

[57] ABSTRACT

A method for the measurement of serum bile acids by ELISA comprising: preparing a bile acid active ester, reacting the ester with a bovine serum albumin solution, dialyzing, and immunizing a mammal other than human being with the dialyzate thus obtained as an antigen to thereby give an anti-bile acid antibody; reacting said active ester with an enzyme to thereby prepare an enzyme-labeled bile acid as an enzyme-labeled antigen; to a secondary antibody-coated plate, adding a dilution of the serum to be assayed, an anti-bile acid antibody solution and an enzyme-labeled antigen solution and reacting these substances followed by the addition of a substrate and the reaction therewith; measuring the absorbance of the reaction mixture and determining the concentration of each bile acid on the basis of the standard curve measured simultaneously; and referring the sum of the concentrations of these bile acids to the total bile acid concentration; and a method for the diagnosis of a liver disease comprising: calculating the concentration ratio of each bile acid from the values measured by the former method; and comparing the concentration ratio thus obtained with the standard level scope of said concentration ratio obtained from healthy subjects are provided.

6 Claims, 6 Drawing Sheets

OTHER PUBLICATIONS

Patent Abstracts of Japan 4(51):53–93628 "Measuring Method for Bile Acid in Blood Using $^{125}I$ Marked Combination Bile Acid Tyrosin Methyl Ester Derivative" (1980).

C. Paul Bianchi, *Chemical Abstracts*, Jun. 1976, vol. 84, No. 25 abstract No. 178092.

C. Paul Bianchi, *Chemical Abstracts*, Nov. 1980, vol. 93, No. 21 abstract No. 200494.

J. Morikawa et al., Patent Abstracts of Japan, Apr. 1980, vol. 4, No. 51, abstract #55–20453.

Rose et al., "Enzyme–Linked Immunosorbent Assay", Manual of Clinical Laboratory Immunology, Third Edition, Chapter 17 (1986) pp. 99–109.

Kano M., Wada H., Matsumoto M., Yamamoto K., Kamano T., Motegi K., Oguchi K. and Kano Y.: Human fecal bile acids and fractions with enzyme–linked immunosorbent assay, Showa Univ. J. Med. Sci., 5: 183 – 191 (1993).

Reddy B.S. and Wynder E.L.: Metabolic epidemiology of colon cancer, Fecal bile acid and neutral sterols in colon cancer patients and patients with adenomatous polyps, Cancer, 39: 2533 – 2539 (1977).

Kumada T., Nakano S., Ohta H., Sasaki T., Kitamura K., Watahiki H., Takeda I., Okuyama S. and Takagi K.; Clinical evaluation on determination of individual bile acids in liver diseases, serum bile acid composition in fulminant hepatitis and acute hepatitis, Kanzhs, 23: 364 – 371 (1982) (English abstract).

Karlaganis G. and Paumgartner G.: Determination of bil acids in serum by capillary gas–liquid chromatography, Clin. Chim. Acta, 92: 19 – 26 (1979).

Maruyama K., Tanimura H. and Hikasa Y.: Analysis of conjugated bile acids in bile by high pressure liquid chromatography, Clin. Chim. Acta, 100: 47 – 54 (1980).

Mashige F., Tanaka N., Maki A., Kamei S. and Yamanaka M.: Direct spectrophotometry of total bile acids in serum, Clinchem., 27: 1352 – 1356 (1981).

Inaguma H., Katagiri K., Tsukada K., Hirose A., Hoshino M., Hayakawa T., Yokochi M., Miyaji M., Ito M. and Takeuchi T.: Serum bile acid composition in fulminant hepatitis, comparative study with acute hepatitis, Nagoya Med. J., 29: 63 – 71 (1984).

Abe K., Yoshiba M. and Sugata F.: Clinical significance of kinetics of serum bile acid fractions in patients with fulminant hepatitis and liver cirrhosis, J. Showa Med. Assoc., 53: 25 – 30 (1993) (English abstract).

Ayaki Y. and Yamasaki K.: In vitro conversion of 7α–hydroxycholesterol to some natural $C_{24}$–bile acis with special reference to chenodeoxycholic acid biogenesis, J. Biochem., 68: 341 – 346 (1970).

FIG. 1.

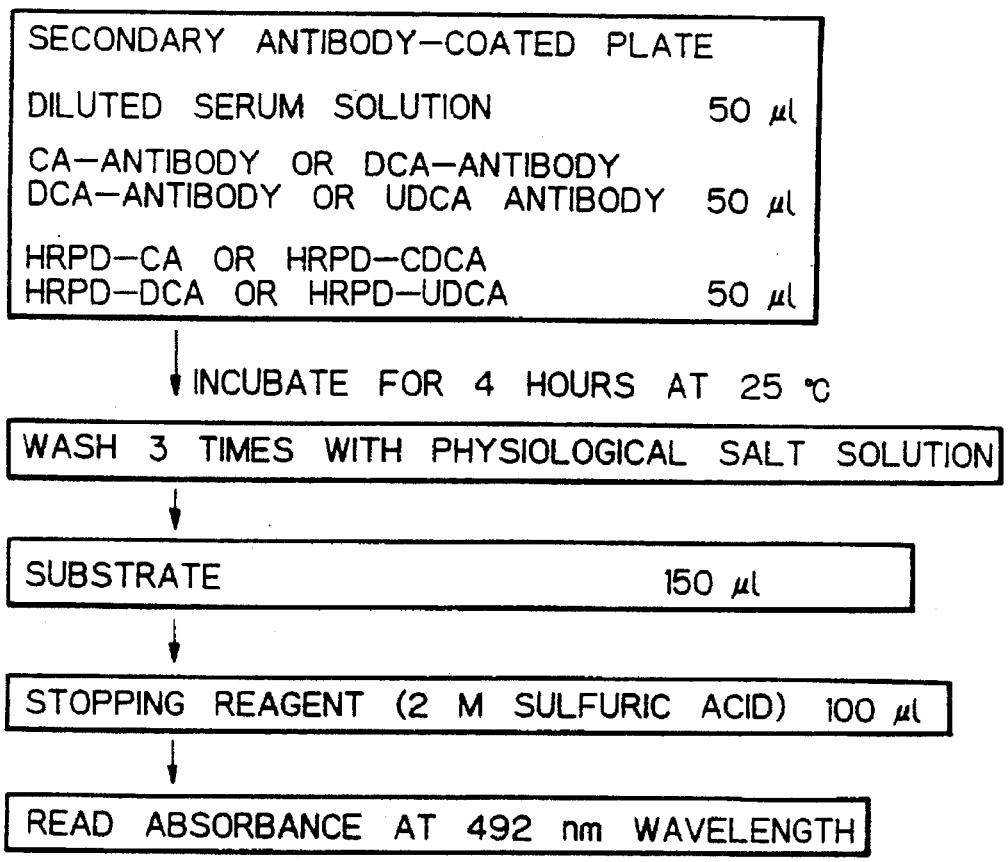

MEASUREMENT OF SERUM CA, CDCA, DCA AND UDCA BY ELISA METHOD CA : CHOLIC ACID, CDCA : CHENODEOXYCHOLIC ACID, DCA : DEOXYCHOLIC ACID, UDCA : URSOCHOLIC ACID, HRP : HORSE RADISH PEROXIDASE. THE COLLECTED SERUM IS INTRODUCED INTO A 0.05 M PHOSPHATE BUFFER (pH 7.4 ; CONTAINING 0.3 M OF SODIUM CHLORIDE, 1 mM OF ETHYLENEDIAMINE TETRAACETIC ACID AND 0.1% OF BOVINE SERUM ALBUMIN), DILUTED 40-FOLD AND THEN EMPLOYED IN A 50 μl PORTION. THE SUBSTRATE IS 0.05 % o-PHENYLENEDIAMINE IN A 0.05 M CITRATE BUFFER (pH 4.4) CONTAINING 0.015 % OF $H_2O_2$

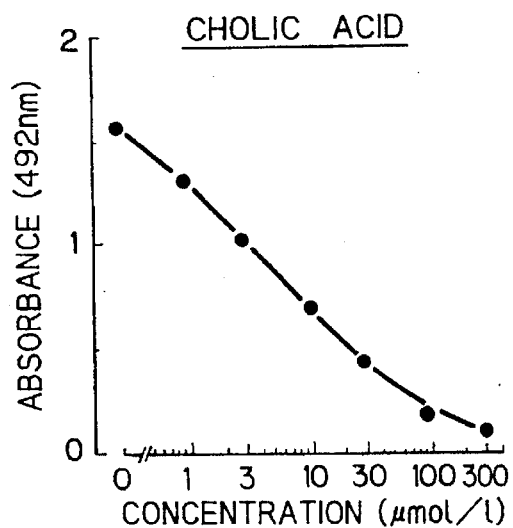
FIG. 2a. CHOLIC ACID
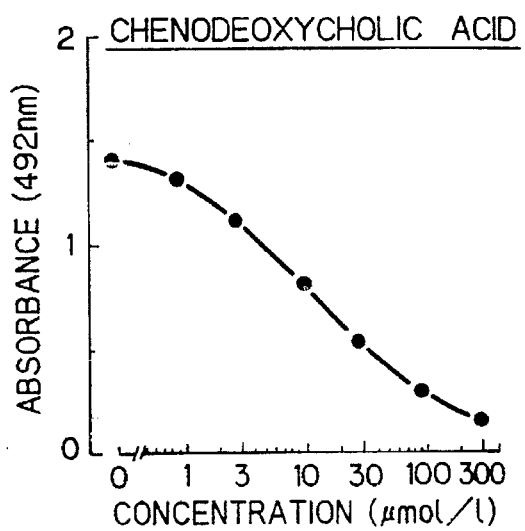
FIG. 2b. CHENODEOXYCHOLIC ACID
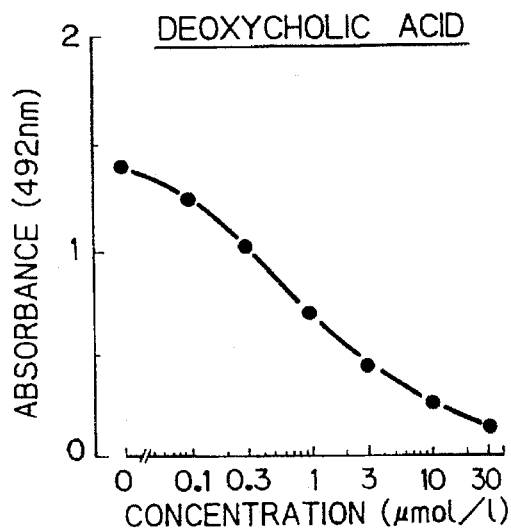
FIG. 2c. DEOXYCHOLIC ACID
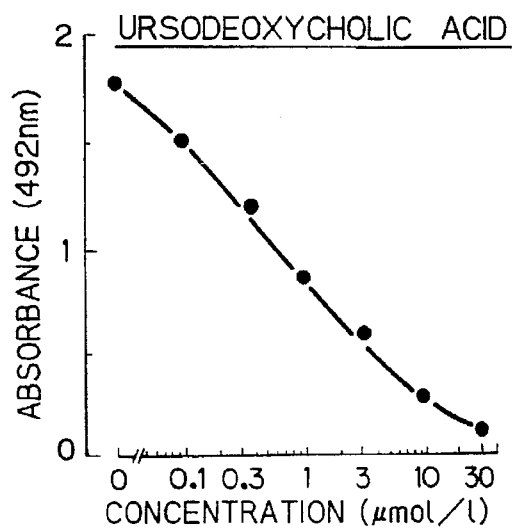
FIG. 2d. URSODEOXYCHOLIC ACID

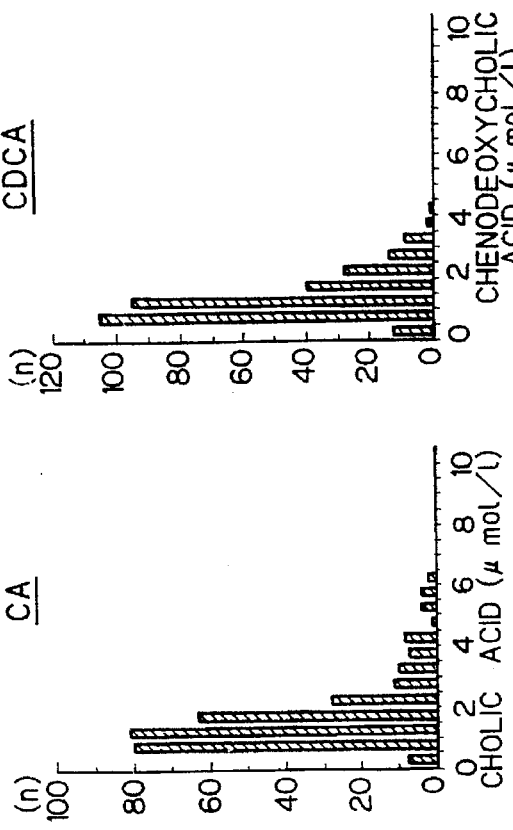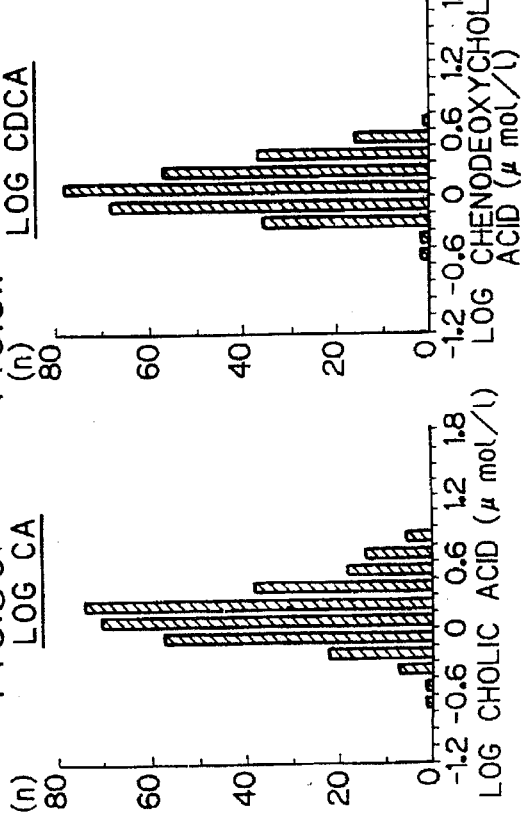

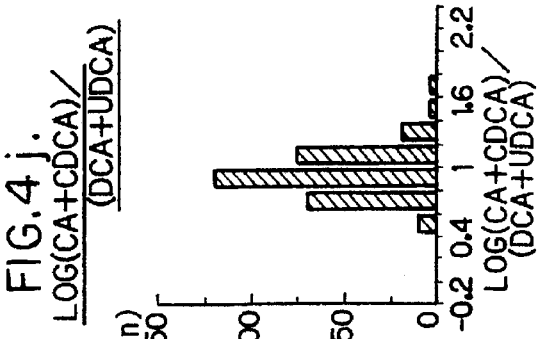
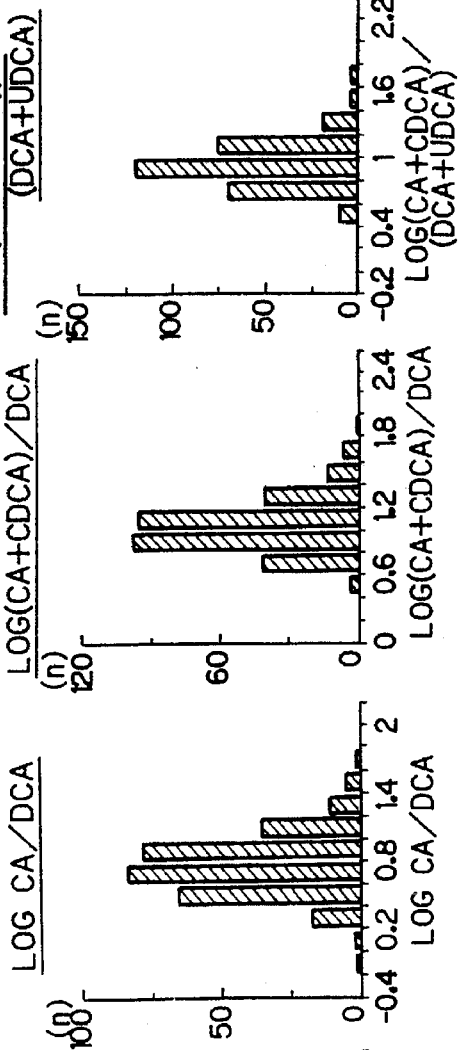
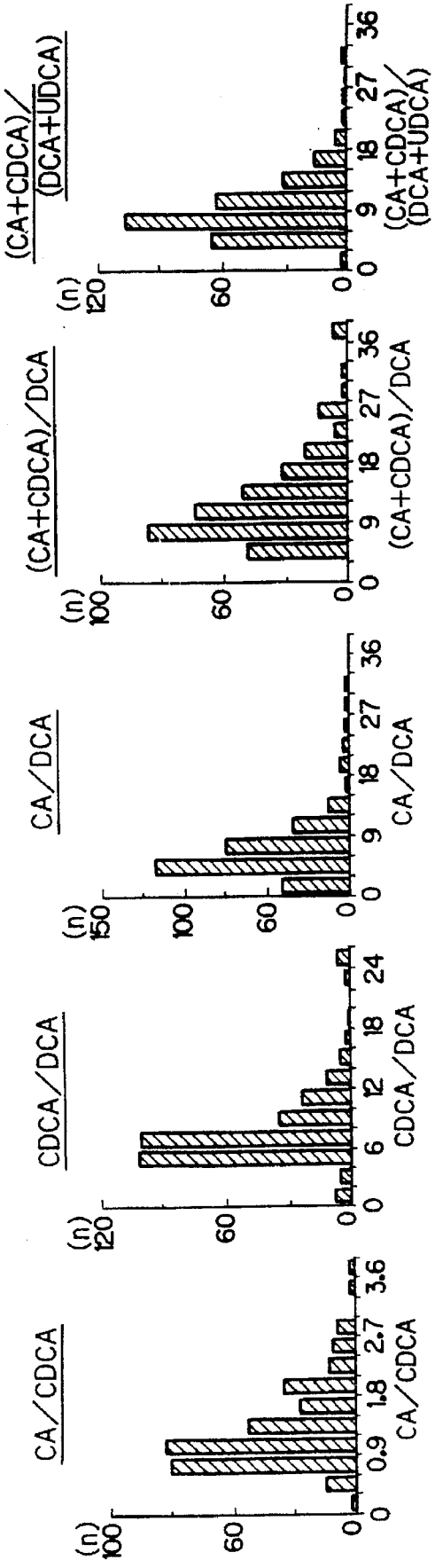
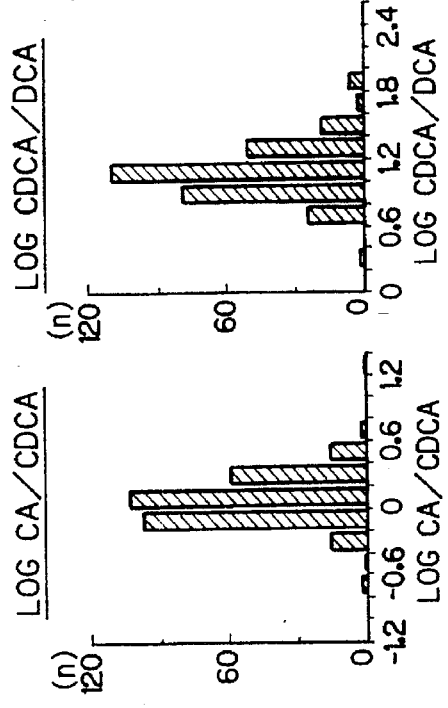

METHOD FOR THE MEASUREMENT OF SERUM BILE ACIDS BY ELISA AND METHOD FOR THE DIAGNOSIS OF LIVER DISEASE

FIELD OF THE INVENTION

This invention relates to a method of ELISA (enzyme linked immunosorbent assay) for the measurement of serum bile acids and a method for the diagnosis of liver disease on the basis of the measurement data thus obtained.

BACKGROUND OF THE INVENTION

Bile acids are one of the major components of bile. In liver cells, cholesterol is formed from acetyl coA (coenzyme A) and further primary bile acids [cholic acid (CA) and chenodeoxycholic acid (CDCA)] are formed therefrom. The primary bile acid conjugated with glycine or taurine undergoes 7α dehydroxylation by enteric bacteria in the intestinal tract and thus secondary bile acids [deoxycholic acid (DCA) and lithocholic acid (LCA)] are formed. At the same time, ursodeoxycholic acid (UDCA) is also formed.

After facilitating the absorption of fat-soluble substances in the intestinal tract, the bile acids are mostly reabsorbed at the end of the ileum and returned to the liver through the portal vein, thus repeating the closed enterohepatic circulation. Bile acids pooled in the body (mainly in the gallbladder and the intestine) amount to about 3 to 5 g. A trace amount of bile acids deviate from the enterohepatic circulation and migrate into the greater blood circulation, which causes a trace bile acid level (about 2 µg/ml) in the peripheral blood of a healthy person in the morning (fasting). The blood bile acid level shows a daily variation in association with meals. Namely, the morning (fasting) blood bile acid level is the lowest and an increase is observed after each meal. After showing a decrease at the bed time, the blood bile acid level returns to the morning (fasting) level.

Regarding bile acids and digestive diseases, there have been reported a number of studies on colon cancer and fecal bile acids [refer to references 1) and 2) in the attached literature list] and blood bile acids and liver diseases [refer to reference 3) in the above-mentioned list]. To study liver diseases accompanied by a trace serum bile acid level, in particular, there have been frequently employed instrumental analyses such as GLC (gas-liquid chromatography) [refer to reference 4) in the above-mentioned list] and HPLC (high performance liquid chromatography) [refer to reference 5) in the above-mentioned list]. However these methods each involve a complicated analytical procedure and thus require a high degree of knowledge and technique.

On the other hand, there has been reported a method for assaying serum bile acids with the use of an enzyme, i.e., 3α-hydroxysteroid dehydrogenase (3α-HSD) [refer to reference 6) in the list]. Although this method has been routinely carried out as a valuable liver function test, it aims at assaying the total bile acids.

As discussed above, instrumental analyses have been widely employed for measuring bile acids as an index to digestive diseases. However these methods each involves a complicated analytical procedure and thus requires a high degree of knowledge and technique. In addition, the method for assaying serum bile acids with the use of an enzyme aims at assaying the total bile acids.

SUMMARY OF THE INVENTION

Under these circumstances, the present inventors have established a method of ELISA which is simple enough to conduct mass assay, comprising:

preparing a bile acid active ester, reacting the ester with a bovine serum albumin solution, dialyzing, and immunizing a mammal other than human being with the dialyzate thus obtained as an antigen to thereby give an anti-bile acid antibody;

reacting said active ester with an enzyme to thereby prepare an enzyme-labeled bile acid as an enzyme-labeled antigen;

to a secondary antibody-coated plate, adding a dilution of the serum to be assayed, an anti-bile acid antibody solution and an enzyme-labeled antigen solution and reacting these substances followed by the addition of a substrate and the reaction therewith;

measuring the absorbance of the reaction mixture and determining the concentration of each bile acid on the basis of the standard curve measured simultaneously; and referring the sum of the concentrations of these bile acids to the total bile acid concentration.

BRIEF DESCRIPTION OF THE DRAWINGS

FIG. 1 is a flow chart which shows a procedure for assaying CA, CDCA, DCA and UDCA in accordance with the ELISA method of the present invention.

FIG. 2A shows the standard curve of CA in accordance with the ELISA method of the present invention.

FIG. 2B shows the standard curve CDCA in accordance with the ELISA method of the present invention.

FIG. 2C shows the standard curve of DCA in accordance with the ELISA method of the present invention.

FIG. 2D shows the standard curve of UDCA in accordance with the ELISA method of the present invention.

FIG. 3A shows the frequency distribution at the levels of serum bile acid CA obtained from healthy subjects (n=307).

FIG. 3B shows the frequency distribution at the levels of serum bile acid CDCA obtained from healthy subjects (n=307).

FIG. 3C shows the frequency distribution at the levels of serum bile acid DCA obtained from healthy subjects (n=307).

FIG. 3D shows the frequency distribution at the levels of serum bile acid UDCA obtained from healthy subjects (n=307).

FIG. 3E shows the logarithmic normal distribution of the levels of the serum bile acid CA obtained from healthy subjects (n=307).

FIG. 3F shows the logarithmic normal distribution of the levels of the serum bile acid CDCA obtained from healthy subjects (n=307).

FIG. 3G shows the logarithmic normal distribution of the levels of the serum bile acid DCA obtained from healthy subjects (n=307).

FIG. 3H shows the logarithmic normal distribution of the levels of the serum bile acid UDCA obtained from healthy subjects (n=307).

FIG. 4A shows the frequency distribution of the ratio CA/CDCA determined from the bile acid levels obtained from healthy subjects (n=307).

FIG. 4B shows the frequency distribution of the ratio CDCA/DCA determined from the bile acid levels obtained from healthy subjects (n=307).

FIG. 4C shows the frequency distribution of the ratio CA/DCA determined from the bile acid levels obtained from healthy subjects (n=307).

FIG. 4D shows the frequency distribution of the ratio CA+CDCA/DCA determined from the bile acid levels obtained from healthy subjects (n=307).

FIG. 4E shows the frequency distribution of the ratio CA+CDCA/DCA+UDCA determined from the bile acid levels obtained from healthy subjects (n=307).

FIG. 4F shows the logarithmic normal distribution of the ratio CA/CDCA determined from the bile acid levels obtained from healthy subjects (n=307).

FIG. 4G shows the logarithmic normal distribution of the ratio CDCA/DCA determined from the bile acid levels obtained from healthy subjects (n=307).

FIG. 4H shows the logarithmic normal distribution of the ratio CA/DCA determined from the bile acid levels obtained from healthy subjects (n=307).

FIG. 4I shows the logarithmic normal distribution of the ratio CA+CDCA/DCA determined from the bile acid levels obtained from healthy subjects (n=307).

FIG. 4J shows the logarithmic normal distribution of the ratio CA+CDCA/DCA+UDCA determined from the bile acid levels obtained from healthy subjects (n=307).

In FIGS. 4A to 6E, CA stands for cholic acid, CDCA stands for chenodeoxycholic acid, DCA stands for deoxycholic acid and UDCA stands for ursocholic acid.

In FIGS. 5A–5E and 6A–6E M stands for mean, TBA stands for the total bile acids (i.e., the sum of CA, CDCA, DCA and UDCA), AH stands for acute hepatitis, AS stands for acute stage, CS stands for convalescence stage, CH stands for chronic hepatitis, LC stands for liver cirrhosis and HCC stands for hepato cellular carcinoma.

DETAILED DESCRIPTION OF THE INVENTION

Figure 5A:
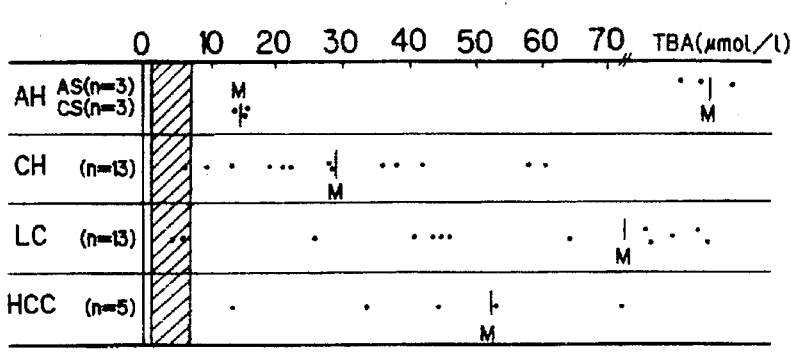
FIG. 5A shows the concentrations of total serum bile acid for patients having the liver diseases: acute hepatitis, chronic hepatitis, liver cirrhosis, hepato cellular carcinoma.

By using the assay method of the present invention as described above, the concentrations of cholic acid, chenodeoxycholic acid, deoxy cholic acid and ursocholic acid (CA, CDCA, DCA and UDCA) of healthy subjects are measured. Then the ratios CA/CDCA, CDCA/DCA, CA/DCA, CA+CDCA/DCA and CA+CDCA/DCA+UDCA are determined and the standard level scope of each ratio is established.

The present inventors have found out that liver diseases can be diagnosed by referring these standard level scopes and thus established a method for the diagnosis of a liver disease comprising:

preparing a bile acid active ester, reacting the ester with a bovine serum albumin solution, dialyzing, and immunizing a mammal other than human being with the dialyzate thus obtained as an antigen to thereby give an anti-bile acid antibody;

reacting said active ester with an enzyme to thereby prepare an enzyme-labeled bile acid as an enzyme-labeled antigen;

to a secondary antibody-coated plate, adding a dilution of the serum to be assayed, an anti-bile acid antibody solution and an enzyme-labeled antigen solution and reacting these substances followed by the addition of a substrate and the reaction therewith;

measuring the absorbance of the reaction mixture and determining the concentration of each bile acid on the basis of the standard curve measured simultaneously;

referring the sum of the concentrations of these bile acids to as the total bile acid concentration and calculating the concentration ratio of each bile acid; and comparing the concentration ratio thus obtained with the standard level scope of said concentration ratio obtained from healthy subjects.

In accordance with the method of the present invention, the serum bile acid levels of patients with acute hepatitis (AH), chronic hepatitis (CH), liver cirrhosis (LC) and hepato cellular carcinoma (HCC) are measured and the concentration ratio of each component is determined similar to the case of the healthy subjects. Then the concentration ratios thus obtained are compared with the standard level scopes from the healthy subjects. After discussing the relation between these data and the pathology of each disease, novel findings are obtained. The results will be described in greater detail in the following example.

Example

Preparation of anti-cholic acid, anti-chenodeoxycholic acid, anti-deoxycholic acid and anti-ursodeoxycholic acid antisera Anti-chenodeoxycholic acid-24-bovine serum albumin-rabbit serum:

(a) Chenodeoxycholic acid (CDCA) (40 mg) was dissolved in 1.0 ml of dioxane. After adding 23 mg of N-hydroxysuccinimide and 38 mg of 1-ethyl-3-(3-dimethylaminopropyl)carbodiimide hydrochloride, the resulting mixture was reacted for 3 hours.

(b) To this reaction mixture were added 4 ml of ethyl acetate and 4 ml of water to thereby extract the bile acid. After removing the aqueous layer, the ethyl acetate layer was dried over sodium acetate and evaporated to dryness. Thus chenodeoxycholic acid active ester was obtained.

(c) Next, the dry product (i.e., chenodeoxycholic acid active ester) was dissolved in 1.0 ml of dimethylformamide and slowly added to 10 ml of a 25 mg/ml bovine serum albumin solution (BSA). Then the mixture was adjusted to pH 7.0 with 1N NaOH.

(d) After being allowed to stand for 30 minutes and then dialyzing against water for one day and night, an antigen (CDCA active ester) was formed.

(e) The antigen thus obtained was given in 1 mg portions for 4 months to a rabbit to thereby immunize the animal. Then the anti-chenodeoxycholic acid thus produced in the body of the rabbit was harvested to thereby give anti-chenodeoxycholic acid-24-bovine serum albumin-rabbit serum (hereinafter referred to as CDCA antibody). The CDCA antibody was diluted 8,000-fold and used in the assay.

Anti-deoxycholic acid-24-bovine serum albumin-rabbit serum:

(a) Deoxycholic acid (DCA) (40 mg) was dissolved in 1.0 ml of dioxane. After adding 23 mg of N-hydroxysuccinimide and 38 mg of 1-ethyl-3-(3-dimethylaminopropyl)carbodiimide hydrochloride, the resulting mixture was reacted for 3 hours.

(b) To this reaction mixture were added 4 ml of ethyl acetate and 4 ml of water to thereby extract the bile acid. After removing the aqueous layer, the ethyl acetate layer was dried over sodium acetate and evaporated to dryness. Thus deoxycholic acid active ester was obtained.

(c) Next, the dry product (i.e., deoxycholic acid active ester) was dissolved in 1.0 ml of dimethylformamide and slowly added to 10 ml of a 25 mg/ml bovine serum albumin solution (BSA). Then the mixture was adjusted to pH 7.0 with 1N NaOH.

(d) After being allowed to stand for 30 minutes and then dialyzing against water for one day and night, an antigen (DCA active ester) was formed.

(e) The antigen thus obtained was given in 1 mg portions for 4 months to a rabbit to thereby immunize the animal. Then the anti-deoxycholic acid thus produced in the body of the rabbit was harvested to thereby give antideoxycholic acid-24-bovine serum albumin-rabbit serum (hereinafter referred to as DCA antibody). The DCA antibody was diluted 20,000-fold and used in the assay.

Anti-ursodeoxycholic acid-24-bovine serum albumin-rabbit serum:

(a) Ursodeoxycholic acid (UDCA) (40 mg) was dissolved in 1.0 ml of dioxane. After adding 23 mg of N-hydroxysuccinimide and 38 mg of 1-ethyl-3-(3-dimethylaminopropyl)carbodiimide hydrochloride, the resulting mixture was reacted for 3 hours.

(b) To this reaction mixture were added 4 ml of ethyl acetate and 4 ml of water to thereby extract the bile acid. After removing the aqueous layer, the ethyl acetate layer was dried over sodium acetate and evaporated to dryness. Thus ursodeoxycholic acid active ester was obtained.

(c) Next, the dry product (i.e., ursodeoxycholic acid active ester) was dissolved in 1.0 ml of dimethylformamide and slowly added to 10 ml of a 25 mg/ml bovine serum albumin solution (BSA). Then the mixture was adjusted to pH 7.0 with 1N NaOH.

(d) After being allowed to stand for 30 minutes and then dialyzing against water for one day and night, an antigen (DCA active ester) was formed.

(e) The antigen thus obtained was given in 1 mg portions for 4 months to a rabbit to thereby immunize the animal. Then the anti-ursodeoxycholic acid thus produced in the body of the rabbit was harvested to thereby give anti-ursodeoxycholic acid-24-bovine serum albumin-rabbit serum (hereinafter referred to as UDCA antibody). The UDCA antibody was diluted 30,000-fold and used in the assay.

Anti-cholic acid-24-bovine serum albumin-rabbit serum:

Anti-cholic acid-24-bovine serum albumin-rabbit serum (hereinafter referred to as CA antibody) was prepared in the following manner with the use of the immunological tolerance.

(a) 15 mg portions of the CDCA active ester and the DCA active ester were each dissolved in 1.0 ml of dimethylformamide and slowly added to 4 ml of a 25 mg/ml poly-D-glutamic acid-D-lysine solution. Then each mixture was allowed to stand for 30 minutes.

(b) After dialyzing against water over day and night, an immunologically tolerant antigen was obtained.

(c) 2 mg of the immunologically tolerant antigen was intraperitoneally injected into a rabbit. From 3 days thereafter, the CA-BSA antigen was administered to the rabbit in 1 mg portions for 4 months to thereby immunize the animal. Thus the CA antibody was obtained.

(d) The CA antibody thus obtained was diluted 5,000-fold and used in the assay.

Preparation of enzyme-labeled CA, enzyme-labeled CDCA, enzyme-labeled DCA and enzyme-labeled UDCA:

2.0 mg of horseradish peroxidase (HRPOD) was dissolved in 0.4 ml of a physiological salt solution containing a 0.1M phosphate buffer (PBS) at pH 7.4. Then 2 µg portions of CA active esters (CDCA active ester, DC active ester and UDCA active ester) were each dissolved in 40 µof dimethylformamide and added to the HRPOD-PBS solution slowly. After 30 minutes, the mixture was dialyzed against 0.1M PBS (pH 7.4) over day and night. The HRPOD-labeled CA (HRPOD-CA) and other enzyme-labeled standard bile acids (HRPOD-CDCA, HRPOD-DCA and HRPOD-UDCA) solutions were diluted 150-fold and then used in the assay.

Assay of bile acids by ELISA:

Table 1 shows the reagents and instruments employed in this method.

TABLE 1

| Reagents and instruments used in the ELISA method | |
|---|---|
| N-hydroxysuccinimide: | Nakarai Chemical Co., Ltd, Kyoto, Japan |
| 1-ethyl-3-(3-dimethyl-amino-propyl)carbodiimide hydrochloride: | Tokyo Kasei Co., Ltd., Tokyo, Japan |
| Standard: | Glycocholic acid (Sigma Chemical Co., Ltd., St. Louis, Mo., USA) Glycochenodeoxycholic acid (Sigma Chemical Co., Ltd., St. Louis, Mo., USA) Glycodeoxycholic acid (Sigma Chemical Co., Ltd., St. Louis, Mo., USA) Glycoursodeoxycholic acid (Sigma Chemical Co., Ltd., St. Louis, Mo., USA) |
| labeling enzyme: | Horseradish peroxidase (Sigma Chemical Co., Ltd., St. Louis, Mo., USA) |
| Substrate: | o-Phenylenediamine (Sigma Chemical Co., Ltd., St. Louis, Mo., USA) |
| Antibody: | Anti-CA-24-BSA-rabbit serum (Self-made) Anti-CDCA-24-BSA rabbit serum (Self-made) Anti-DCA-24-BSA-rabbit serum (Self-made) Anti-UDCA-24-BSA-rabbit serum (Self-made) |

TABLE 1-continued

Reagents and instruments used in the ELISA method

| | |
|---|---|
| Secondary antibody: | Anti-rabbit IgG goat serum (Eiken Chemical Co., Ltd., Tokyo, Japan) |
| Plate: | Sumilon ELISA plate (MS-8496F, Sumitomo Bakelite Co., Ltd., Tokyo, Japan) |
| Spectrophotometer: | $V_{max}$ (Molecular Devices Company, Palo Alto, Ca., USA) |
| Washing instrument: | ULTRAWASH-II (DYNATECK Company, Channel Islands, England) |

Every specimen employed in the assay was collected in the morning (fasting). After separating, the serum was stored at −20° C. or below. In accordance with the procedure shown in FIG. 1, 50 µl portions of a diluted serum, an anti-bile acid antibody solution and an enzyme-labeled antigen solution were added to the secondary antibody-coated plate and reacted at 25° C. for 4 hours. After washing, the substrate was further added thereto and reacted at 25° C. for 30 minutes. Then a stopping reagent was added and the absorbance was measured with the use of a 492 nm filter. Then the levels of CA, CDCA, DCA and UDCA were determined on the basis of standard curves measured simultaneously. The sum of the levels of these 4 bile acids was referred to as the total bile acid level (TBA).

The subjects involved 307 healthy persons aged from 18 to 69 (average age: 43.3, 187 male subjects of 44.6 in average age and 120 female ones of 41.3 in average age). As Table 2 shows, the patients with liver diseases involved 6 cases of acute hepatitis, 13 cases of chronic hepatitis, 13 cases of liver cirrhosis and 5 cases of hepato cellular carcinoma. The significant difference was determined by the t-calibration test.

TABLE 2

List of patients with liver diseases

| Subject | | n | Sex | | Age (mean ± SD) | Etilogy | (n) |
|---|---|---|---|---|---|---|---|
| AH | AS | 3 | M | 3 | 56.3 ± 9.0 | C | (2) |
| | | | | | | B | (1) |
| | CS | 3 | M | 3 | 50.7 ± 12.8 | C | (2) |
| | | | | | | A | (1) |
| CH | | 13 | M | 10 | 59.0 ± 7.9 | B | (2) |
| | | | F | 3 | | B + C | (1) |
| | | | | | | C | (10) |
| LC | | 13 | M | 11 | 53.5 ± 8.0 | B | (1) |
| | | | F | 2 | | C | (9) |
| | | | | | | Alcohol | (3) |
| HCC | | 5 | M | 4 | 57.2 ± 6.2 | C | (5) |
| | | | F | 1 | | | |

M: male, F: female, AH: acute hepatitis, AS: acute stage, CS: convalescence stage, CH: chronic hepatitis, LC: liver cirrhosis, HCC: hepato cellular carcinoma.

RESULTS:

FIGS. 2A, 2B, 2C and 2D show the standard curves of CA, CDCA, DCA and UDCA in this ELISA method. These standard curves are typical ones of ELISA. Also double measurement data are satisfactory ones.

TABLE 3

Cross-reaction rates between bile acids and antibodies

| | Antibody (%) | | | |
|---|---|---|---|---|
| | anti-CA | anti-CDCA | anti-DCA | anti-UDCA |
| Cholic acid | 100 | 0.9 | 1.6 | 0.1> |
| Glycocholic acid | 164 | 0.4 | 3.4 | 0.1> |
| Taurocholic acid | 210 | 0.4 | 4.9 | 0.1> |
| Chenodeoxycholic acid | 1.5 | 100 | 0.2 | 0.1 |
| Glycochenodeoxycholic acid | 2.9 | 178 | 0.6 | 0.2 |
| Taurochenodeoxycholic acid | 3.5 | 183 | 0.8 | 0.1 |
| Deoxycholic acid | 3.5 | 0.1> | 100 | 0.1> |
| Glycodeoxycholic acid | 2.0 | 0.1> | 184 | 0.1> |
| Taurodeoxycholic acid | 4.1 | 0.1> | 192 | 0.1> |
| Ursodeoxycholic acid | 0.1> | 0.1> | 0.1> | 100 |
| Glycoursodeoxycholic acid | 0.1> | 0.1> | 0.1 | 111 |
| Tauroursodeoxycholic acid | 0.2 | 0.1> | 0.1 | 146 |
| Lithocholic acid | 0.1 | 0.1> | 1.7 | 0.1 |
| Glycolithocholic acid | 0.1 | 0.1> | 3.2 | 0.2 |
| Taurolithocholic acid | 0.1 | 0.1> | 2.3 | 0.2 |

CA: cholic acid, CDCA: chenodeoxycholic acid, DCA: deoxycholic acid, UDCA: ursodeoxycholic acid.

Table 3 shows the cross-reaction rates between bile acids and antibodies, i.e., the cross-reaction rates of the CA-antibody, the CDCA-antibody, the DCA-antibody and the UDCA-antibody with each bile acid. In the case of the CA-antibody, the cross-reaction rate with free CA was 100%, while those with the glycine and taurine conjugates were respectively 164% and 210%. Similarly, those of CDCA ranged from 1.5 to 3.5%. The cross reaction rates with DCA (i.e., a secondary bile acid) ranged from 2.0 to 4.1%, while that with lithocholic acid (LCA) was 0.1%.

In the case of the CDCA-antibody, the cross-reaction rate with free CDCA was 100%, while those with the glycine and taurine conjugates were 178% and 183% respectively. cross-reaction rates with CA ranged from 0.4 to 0.9%, while those with LCA and UDCA were not more than 0.1%.

In the case of the DCA-antibody, the cross-reaction rate with free DCA was 100%, while those with the glycine and taurine conjugates were 184% and 192% respectively. Similarly, the cross-reaction rates with CA, CDCA and LCA were respectively not more than 4.9%, not more than 0.8% and not more than 3.2%.

In the case of the UDCA-antibody, the cross-reaction rate with free UDCA was 100%, while those with the glycine and taurine conjugates were 111% and 146% respectively. The cross-reaction rates with other components were each 0.2% or below.

The cross-reaction rate of the CDCA-antibody of the primary bile acid with the secondary bile acid DCA was not more than 0.1%. Similarly, that with the CA-antibody was not more than 4.1%. The cross-reaction rate of the DCA-antibody of the secondary bile acid with the primary bile acid CDCA was not more than 0.8% and that with CA was not more than 4.9%, each showing a low ratio. Thus almost satisfactory results were obtained regarding these bile acid antibodies.

The following Table 4 shows the within-run reproducibilities and the between-day reproducibilities of samples I and II of different concentrations.

TABLE 4

| | Reproducibilities of data from patients' sera | | | |
|---|---|---|---|---|
| | Within-run reproducibility | | Between-day reproducibility | |
| Sample (n = 10) | M ± SD [μmol/l] | CU (%) (n = 10) | M ± SD [μmol/l] | CU (%) |
| CA | | | | |
| Sample I | 8.93 ± 0.518 | 5.8 | 8.97 ± 0.657 | 7.3 |
| II | 64.93 ± 3.505 | 5.4 | 63.61 ± 5.379 | 8.4 |
| CDCA | | | | |
| Sample I | 5.53 ± 0.427 | 7.7 | 5.68 ± 0.529 | 9.3 |
| II | 47.12 ± 2.87 | 6.1 | 47.02 ± 3.535 | 7.5 |
| DCA | | | | |
| Sample I | 0.38 ± 0.031 | 8.3 | 0.38 ± 0.041 | 10.9 |
| II | 1.60 ± 0.118 | 7.4 | 1.62 ± 0.150 | 9.2 |
| UDCA | | | | |
| Sample I | 2.73 ± 0.096 | 3.5 | 2.68 ± 0.197 | 7.3 |
| II | 8.14 ± 0.254 | 3.1 | 8.15 ± 0.271 | 3.3 |

CA: cholic acid, CDCA: chenodeoxycholic acid DCA: deoxycholic acid, UDCA: ursodeoxycholic acid C.V.: coefficient of variation Regarding the within-run reproducibilities, the same tendency independent of concentration was observed. UDCA achieved the best results followed by CA. Regarding the between-day reproducibilities, a similar tendency was observed. Thus the obtained data were almost satisfactory ones.

To examine effects of storage conditions, the patients' samples I and II with different concentrations were stored at −20°, 4° and 25° C. Although the DCA and UDCA samples II showed somewhat decreases, it was found out that these samples remained relatively stable under each condition within 14 days, as shown by Table 5.

TABLE 5

| | | | Effects of storage conditions on serum bile acids from patients | | | | | |
|---|---|---|---|---|---|---|---|---|
| Bile acid | Sample | Storage temp. | Storage time (days) | | | | | |
| (μmol/l) | No. | (°C.) | fresh | 1 | 3 | 7 | 14 | mean ± S.D |
| CA | I | −20 | 9.0 | 8.4 | 9.5 | 8.2 | 8.4 | 8.7 ± 0.44 |
| | | 4 | 9.0 | 8.5 | 9.2 | 9.0 | 8.8 | 8.9 ± 0.22 |
| | | 25 | 9.0 | 8.6 | 8.8 | 9.3 | 8.8 | 8.9 ± 0.22 |
| | II | −20 | 63.6 | 62.7 | 61.0 | 66.5 | 64.7 | 63.7 ± 1.69 |
| | | 4 | 63.6 | 63.5 | 61.5 | 64.3 | 62.5 | 63.1 ± 0.89 |
| | | 25 | 63.6 | 64.1 | 66.9 | 69.7 | 62.7 | 65.4 ± 2.35 |
| CDCA | I | −20 | 5.4 | 5.2 | 5.0 | 5.5 | 5.4 | 5.3 ± 0.16 |
| | | 4 | 5.4 | 5.2 | 4.9 | 5.1 | 5.0 | 5.1 ± 0.16 |
| | | 25 | 5.4 | 5.7 | 5.1 | 5.7 | 5.6 | 5.5 ± 0.21 |
| | II | −20 | 47.7 | 45.2 | 48.8 | 46.3 | 47.2 | 47.0 ± 1.12 |
| | | 4 | 47.7 | 44.5 | 46.8 | 44.5 | 46.4 | 46.0 ± 1.17 |
| | | 25 | 47.7 | 46.6 | 46.5 | 43.6 | 45.1 | 45.9 ± 1.29 |
| DCA | I | −20 | 0.38 | 0.35 | 0.36 | 0.35 | 0.32 | 0.35 ± 0.02 |
| | | 4 | 0.38 | 0.37 | 0.34 | 0.41 | 0.34 | 0.37 ± 0.02 |
| | | 25 | 0.38 | 0.34 | 0.33 | 0.33 | 0.30 | 0.34 ± 0.02 |
| | II | −20 | 1.65 | 1.64 | 1.52 | 1.41 | 1.31 | 1.51 ± 0.12 |
| | | 4 | 1.65 | 1.55 | 1.41 | 1.38 | 1.28 | 1.45 ± 0.12 |
| | | 25 | 1.65 | 1.37 | 1.31 | 1.30 | 1.22 | 1.37 ± 0.14 |
| UDCA | I | −20 | 2.69 | 2.73 | 2.64 | 2.54 | 2.51 | 2.62 ± 0.08 |
| | | 4 | 2.69 | 2.59 | 2.60 | 2.67 | 2.62 | 2.63 ± 0.04 |
| | | 25 | 2.69 | 2.60 | 2.55 | 2.77 | 2.62 | 2.65 ± 0.07 |
| | II | −20 | 8.06 | 7.69 | 7.35 | 7.84 | 7.88 | 7.76 ± 0.22 |
| | | 4 | 8.06 | 7.58 | 7.88 | 7.92 | 7.70 | 7.83 ± 0.15 |
| | | 25 | 8.06 | 7.81 | 7.54 | 7.64 | 7.91 | 7.79 ± 0.17 |

CA: cholic acid, CDCA: chenodeoxycholic acid, DCA: deoxycholic acid, UDCA: ursodeoxycholic acid.

Table 6 shows the standard level scopes of bile acid levels in healthy individuals. FIGS. 3A, 3B, 3C, 3D, 3E, 3F, 3G and 3H show the frequency distribution of serum bile acids from 307 healthy subjects. FIGS. 4A, 4B, 4C, 4D, 4E, 4F, 4G, 4H and 4J show the frequency distributions of the CA/CDCA ratio, the CDCA/DCA ratio, the CA/DCA ratio, the CA+CDCA/DCA ratio and the CA+CDCA/DCA+ UDCA ratio determined from these bile acid levels. Each of these frequency distributions is not a Gaussian distribution but a logarithmic normal distribution. After normalizing the data, the mean ±2SD were determined. Table 6 shows the results.

TABLE 6

| | Bile acid levels of healthy individuals | | |
|---|---|---|---|
| | All healthy subject, n = 307 mean (−2SD−+2SD) | Males, n = 187 mean (−2SD−+2SD) | Females, n = 120 mean (−2SD−+2SD) |
| CA [µmol/l] | 1.39 (0.51–3.79) | 1.29 (0.44–3.80) | 1.52 (0.62–3.75) |
| CDCA [µmol/l] | 1.22 (0.47–3.18) | 1.27 (0.52–3.07) | 1.15 (0.40–3.32) |
| DCA [µmol/l] | 0.27 (0.12–0.58) | 0.26 (0.11–0.60) | 0.24 (0.10–0.57) |
| UDCA [µmol/l] | 0.051 (0.017–0.151) | 0.049 (0.11–0.141) | 0.052 (0.019–0.145) |
| TBA [µmol/l] | 2.93 (1.29–6.65) | 2.83 (1.29–6.21) | 2.99 (1.26–7.12) |
| CA/CDCA ratio | 1.18 (0.64–2.19) | 1.04 (0.46–2.35) | 1.38 (0.63–3.01) |
| CDCA/DCA ratio | 4.64 (1.87–11.56) | 4.47 (1.84–12.21) | 4.40 (1.98–9.75) |
| CA/DCA ratio | 5.38 (1.82–15.90) | 5.19 (1.63–16.58) | 6.28 (2.73–14.42) |
| CA + CDCA/DCA ratio | 10.36 (4.09–26.22) | 9.85 (3.56–27.21) | 10.99 (4.97–24.34) |
| CA + CDCA/DCA + UDCA ratio | 8.34 (3.74–18.57) | 7.98 (3.44–18.51) | 8.87 (4.41–17.84) |

Values are expressed in the standard level (mean ± 2SD) of each bile acid and the standard ratio (mean ± 2SD) obtained by calculation. CA: cholic acid, CDCA: chenodeoxycholic acid, DCA: deoxycholic acid, UDCA: ursodeoxycholic acid, TBA: total bile acids (CA + CDCA + DCA + UDCA).

Table 6 shows the total serum bile acids (TBA) and the bile acid concentration of each fraction. As described above, the sum of the data of the fractions was referred to as TBA. Compared with the standard level scope [2.93 (1.29 to 6.65 µmol/l)] obtained from 307 healthy subjects (187 males and 120 females), the patients with acute hepatitis at the acute stage showed TBA of 293.3±148.2 µmol/l (mean ±SD), those at the convalescence stage showed TBA of 14.6±14.6 µmol/l, those with chronic hepatitis showed TBA of 29.3±16.3 µmol/l, those with liver cirrhosis showed TBA of 71.2±58.6 µmol/l and those with hepato cellular carcinoma showed TBA of 52.5±35.4 µmol/l. Namely, the TBA levels of these patients were each significantly higher (P<0.01) than that of the healthy subjects. In particular, the patients with acute hepatitis at the acute stage, liver cirrhosis and hepato cellular carcinoma showed remarkably high TBA levels.

Figure 5B:
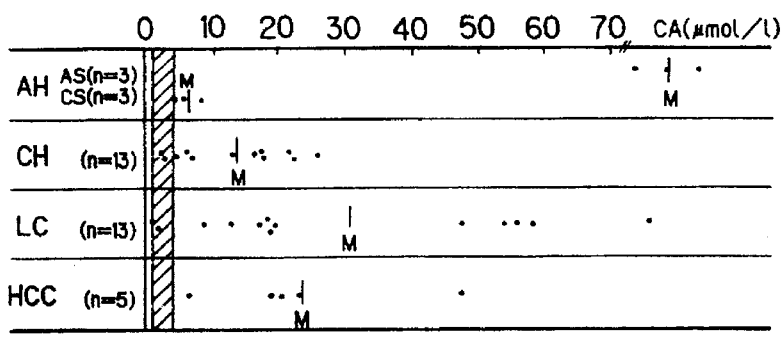
FIG. 5B shows the serum bile acid CA concentrations for patients with the liver diseases: acute hepatitis, chronic hepatitis, liver cirrhosis, hepato cellular carcinoma.
Figure 5C:
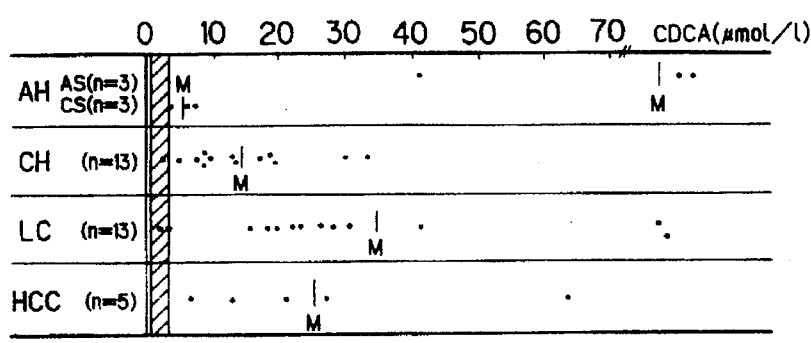
FIG. 5C shows the serum bile acid CDCA concentrations for patients with the liver diseases: acute hepatitis, chronic hepatitis, liver cirrhosis, hepato cellular carcinoma.
Figure 5D:
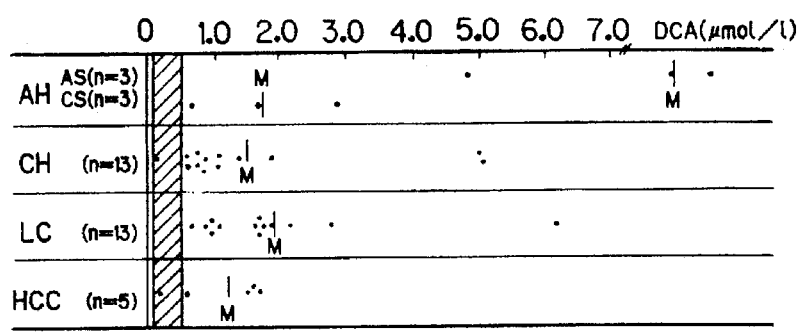
FIG. 5D shows the serum bile acid DCA concentrations for patients with the liver diseases: acute hepatitis, chronic hepatitis, liver cirrhosis, hepato cellular carcinoma.
Figure 5E:
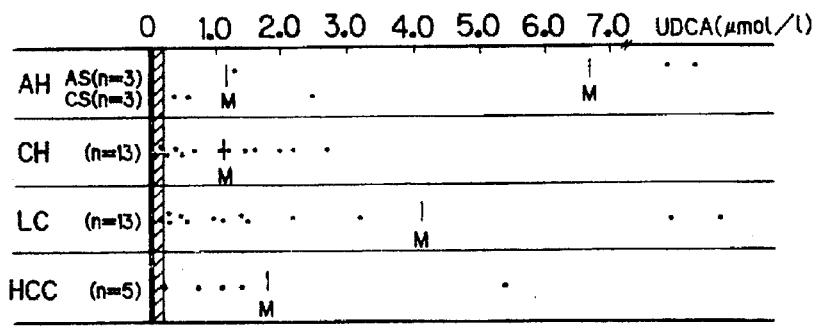
FIG. 5E shows the serum bile acid UDCA concentrations for patients with the liver diseases: acute hepatitis, chronic hepatitis, liver cirrhosis, hepato cellular carcinoma.

As FIGS. 5A, 5B, 5C, 5D and 5E show, each disease group showed a significantly higher (P<0.01) level of each fraction in comparison with that of the group of the healthy individuals, though no significant difference was observed among disease groups. In 37 cases of liver diseases, 33 cases (89.2%) showed abnormally high CA levels excluded from the standard level scope. Similarly, 34 cases (91.9%), 35 cases (94.6%) and 36 cases (97.3%) showed abnormally high CDCA, DCA and UDCA levels respectively.

Discussion on ratios determined from fraction levels
CA/CDA ratio

Figure 6A:
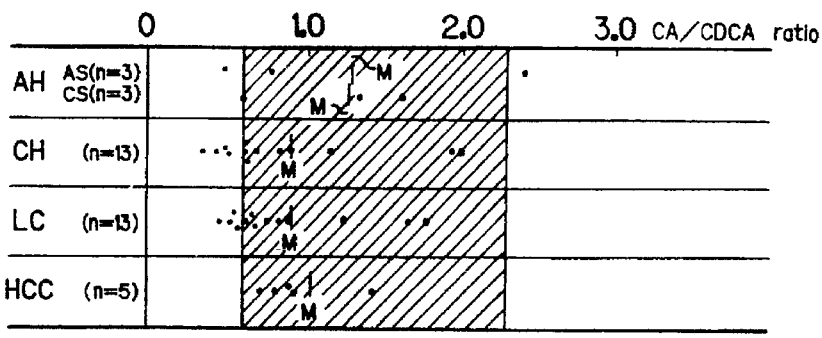
FIG. 6A shows the serum bile acid concentration ratio CA/CDCA of patients with liver diseases: acute hepatitis, chronic hepatitis, liver cirrhosis, hepato cellular carcinoma.
Figure 6B:
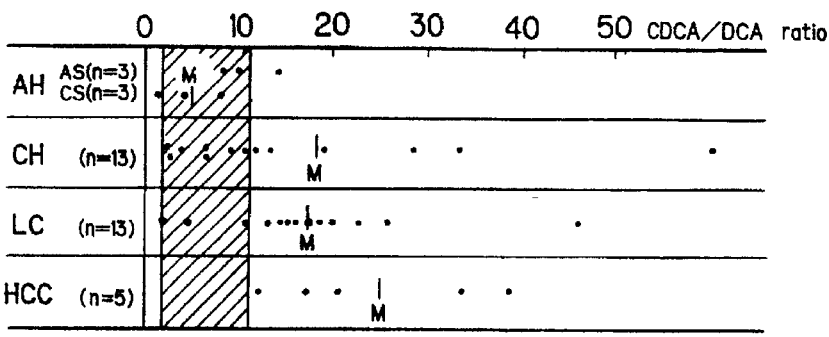
FIG. 6B shows the serum bile acid concentration ratio CDCA/DCA of patients with liver diseases: acute hepatitis, chronic hepatitis, liver cirrhosis, hepato cellular carcinoma.
Figure 6C:
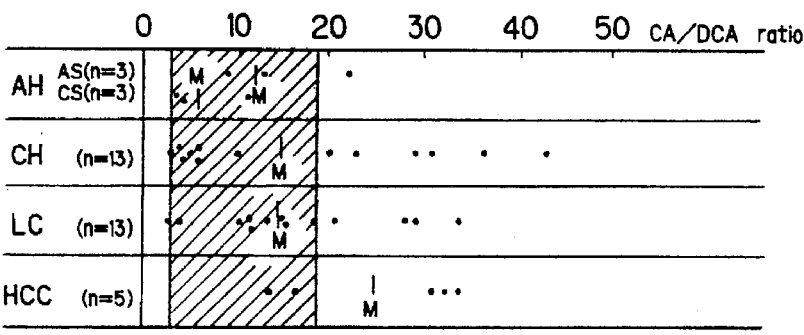
FIG. 6C shows the serum bile acid concentration ratio CA/DCA of patients with liver diseases: acute hepatitis, chronic hepatitis, liver cirrhosis, hepato cellular carcinoma.
Figure 6D:
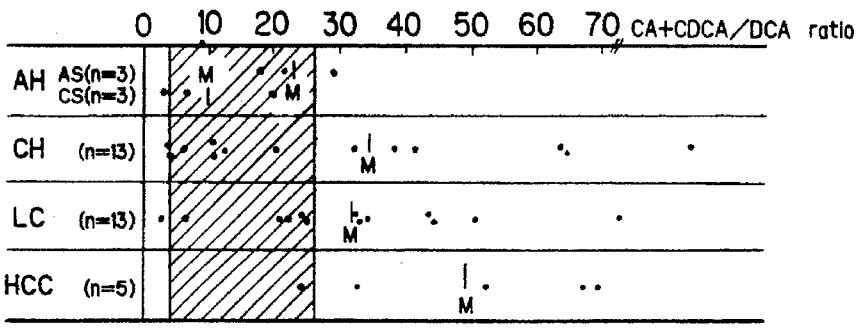
FIG. 6D shows the serum bile acid concentration ratio CA+CDCA/DCA of patients with liver diseases: acute hepatitis, chronic hepatitis, liver cirrhosis, hepato cellular carcinoma.
Figure 6E:
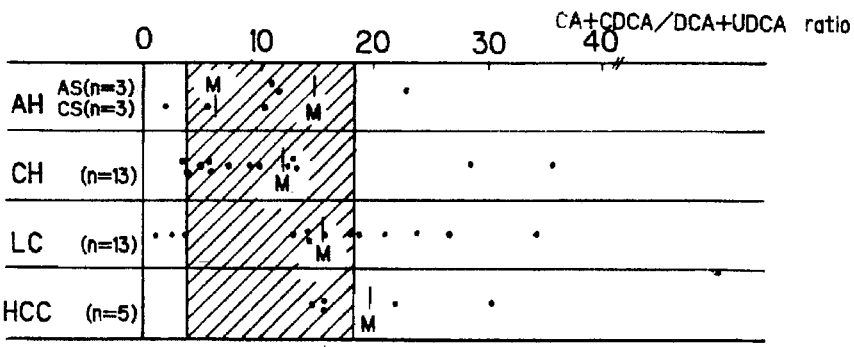
FIG. 6E shows the serum bile acid concentration ratio CA+CDCA/DCA+UDCA of patients with liver diseases: acute hepatitis, chronic hepatitis, liver cirrhosis, hepato cellular carcinoma.

Regarding the CA/CDCA ratios, nearly all the cases fall within the standard level scope, as FIGS. 6A, 6B, 6C, 6D and 6E show. However 4 chronic hepatitis cases and 4 liver cirrhosis cases show CA/CDCA ratios less than the lower limit of the standard level. 10 liver cirrhosis cases (76.9%), among 13, show CA/CDCA ratios of 1.0 or lower.

The standard level obtained from the healthy individuals is 1.16 (0.64 to 2.19; mean±2SD), while those (mean±SD) of the acute hepatitis (acute stage) group, the acute hepatitis (convalescence stage) group, the chronic hepatitis group, the liver cirrhosis group and the hepato cellular carcinoma group are respectively 1.26±0.86, 1.23±0.44, 0.89±0.52, 0.90±0.42 and 1.00±0.25. Although no significant difference is observed among the liver diseases groups, the liver cirrhosis group shows a significant difference (P<0.05) from the group of the healthy individuals.

CDCA/DCA ratio

TABLE 7

| Serum bile acid fraction levels and ratios in patients with AH, CH, LC and HCC | | | | | | |
|---|---|---|---|---|---|---|
| Subjects | n | CA (µmol/l) | CDCA (µmol/l) | DCA (µmol/l) | UDCA (µmol) | TBA (µmol) |
| AH  AS | 3 | 103.5 ± 25.4 | 117.5 ± 54.8 | 10.60 ± 4.92 | 6.75 ± 3.90 | 293.3 ± 148.2 |
| CS | 3 | 6.1 ± 1.6 | 5.5 ± 1.5 | 1.77 ± 0.89 | 1.18 ± 0.94 | 14.6 ± 14.6 |
| CH | 13 | 12.4 ± 7.9 | 14.3 ± 8.8 | 1.57 ± 1.56 | 1.11 ± 0.80 | 29.3 ± 16.3 |
| LC | 13 | 30.5 ± 25.1 | 34.7 ± 34.0 | 1.89 ± 1.37 | 4.12 ± 8.43 | 71.2 ± 58.6 |
| HCC | 5 | 23.3 ± 13.4 | 26.3 ± 19.9 | 1.13 ± 0.61 | 1.78 ± 1.85 | 52.5 ± 35.4 |

| Subjects | n | CA/CDCA | CDCA/DCA | CA/DCA | CA + CDCA/ DCA | CA + CDCA/ DCA + UDCA |
|---|---|---|---|---|---|---|
| AH  AS | 3 | 1.26 ± 0.86 | 10.9 ± 2.6 | 12.0 ± 6.1 | 22.9 ± 4.6 | 15.3 ± 5.5 |
| CS | 3 | 1.23 ± 0.44 | 4.5 ± 2.9 | 5.4 ± 4.4 | 9.9 ± 7.1 | 5.9 ± 3.6 |
| CH | 13 | 0.89 ± 0.52 | 18.6 ± 23.2 | 15.5 ± 13.9 | 34.2 ± 35.3 | 11.8 ± 9.4 |
| LC | 13 | 0.90 ± 0.42 | 17.8 ± 10.7 | 15.0 ± 9.2 | 31.9 ± 18.0 | 16.0 ± 9.3 |
| HCC | 5 | 1.00 ± 0.25 | 25.1 ± 10.4 | 24.1 ± 8.7 | 49.2 ± 18.0 | 19.8 ± 5.9 |

Values are expressed in mean ± 2SD. CA: cholic acid, CDCA: chenodeoxycholic acid, DCA: deoxycholic acid, UDCA: ursodeoxycholic acid, TBA: total bile acids (CA + CDCA + DCA + UDCA), AH: acute hepatitis, AS: acute stage, CS: convalescence stage, CH: chronic hepatitis, LS: liver cirrhosis, HCC: hepato cellular carcinoma.

Regarding the CDCA/DCA ratios, the standard level is 4.64 (1.87 to 11.56; mean±2SD), while those (mean±SD) of the acute hepatitis (acute stage) group, the chronic hepatitis group, the liver cirrhosis group and the hepato cellular carcinoma group are respectively 10.9±2.6, 18.6±23.2, 17.8±10.7 and 25.1±10.4, thus being significantly higher ($P<0.01$) than the group of the healthy individuals.

On the other hand, the incidences of abnormal cases showing a CDCA/DCA ratio exceeding the upper limit of the standard level are as follows: 1 acute hepatitis case among 6 (16.7%), 6 chronic hepatitis cases among 13 (46.1%), 10 liver cirrhosis cases among 13 (76.9%) and 5 hepato cellular carcinoma cases among 5 (100%). Although no significant difference is observed among the liver disease groups, the incidence of the abnormal cases is associated with the severity of the disease and thus seemingly reflects the differences in severity among the disease groups.

CA/DCA ratio

Regarding the CA/DCA ratios, the standard level is 5.38 (1.82 to 15.90; mean±2SD), while those (mean±SD) of the acute hepatitis (acute stage) group, the acute hepatitis (convalescence stage) group, the chronic hepatitis group, the liver cirrhosis group and the hepato cellular carcinoma group are respectively 12.0±6.1, 5.4±4.4, 15.5±13.9, 15.0±9.2 and 24.1±8.7. Except the acute hepatitis (convalescence stage) group, the liver disease groups show CA/DCA ratios significantly higher ($P<0.01$) than that of the group of the healthy individuals, though no significant difference was observed among these disease groups.

CA+CDCA/DCA ratio

Regarding the CA+CDCA/DCA ratios, the standard level is 10.36 (4.09 to 26.22; mean±2SD), while those (mean±SD) of the acute hepatitis (acute stage) group, the acute hepatitis (convalescence stage) group, the chronic hepatitis group, the liver cirrhosis group and the hepato cellular carcinoma group are respectively 22.9±4.6, 9.9±7.1, 34.2±35.3, 31.9±18.0 and 49.2±18.0. The chronic hepatitis, liver cirrhosis and hepato cellular carcinoma groups show CA+CDCA/DCA ratios significantly higher ($P<0.01$) than that of the group of the healthy individuals. Also, 6 chronic hepatitis cases among 13 (46.2%), 7 liver cirrhosis cases among 13 (53.9%) and 4 hepato cellular carcinoma cases among 5 (80.0%) show CA+CDCA/DCA ratios exceeding the upper limit of the standard level, though this tendency is not so remarkable as that of the CDCA/DCA ratios.

CA+CDCA/DCA+UDCA ratio

Regarding the CA+CDCA/DCA+UDCA ratios, the standard level is 8.34 (3.74 to 18.57; mean±2SD), while those (mean±SD) of the acute hepatitis (acute stage) group, the acute hepatitis (convalescence stage) group, the chronic hepatitis group, the liver cirrhosis group and the hepato cellular carcinoma group are respectively 15.3±5.5, 5.9±3.6, 11.8±94, 16.0±9.3 and 19.8±5.9. The liver cirrhosis and hepato cellular carcinoma groups show CA+CDCA/DCA+UDCA ratios significantly higher ($P<0.01$) than that of the group of the healthy individuals, though no significant difference was observed among these disease groups.

In recent years, chronic hepatitis is induced in Japan by hepatitis C virus at a ratio of about 60 to 70% and by hepatitis B virus at a ratio of 20 to 30%. It is estimated that 10 to 20% of patients with chronic hepatitis undergo progression into liver cirrhosis and more than 50% of them also suffer from hepato cellular carcinoma.

We have established a method of ELISA for assaying fractions of serum bile acids, i.e., CA, CDCA, DCA and UDCA and set the standard level of each fraction with the use of the data obtained from healthy individuals. Based on these data thus obtained, we have further determined the ratios CA/CDCA, CDCA/DCA, CA/DCA, CA+CDCA/DCA and CA+CDCA/DCA+UDCA and set standard levels therefor. Then we have discussed a possibility to examine differences in the pathology of liver disorders.

Although the assay of serum TBA cannot always achieve a high ratio of detecting abnormalities in the case of mild liver disorders, it is advantageous in that an abnormally high level means no false positive reaction, though a false negative reaction is observed in some cases. That is to say, a case with an abnormally high TBA level is associated with liver disorders without fail.

In nearly all the cases of the patients with liver diseases employed in this study, both of TBA and the bile acid fractions show high values exceeding the standard levels. These facts have revealed the dynamics of serum bile acids, namely, liver disorders cause abnormal increases in TBA components (i.e., CA, CDCA, DCA, UDCA, etc.) and, in its turn, elevate the TBA level. However the tendency toward higher levels of bile acid fractions and TBA is observed in common to liver diseases, which makes the diagnosis of each disease difficult.

On the other hand, the rapid breakage of liver cells causes disorders in the intake of bile acids in the liver or the excretion thereof into the bile and thus induces an increase in the serum TBA level [refer to reference 7) in the attached literature list]. Also, an increase in the TBA level is observed in the case of liver cirrhosis.

In our study, it is observed that CA, CDCA, DCA and UDCA are abnormally increased and consequently an abnormally high TBA level is achieved in the acute stage of acute hepatitis. A similar tendency toward high levels is observed in the case of liver cirrhosis too. This is seemingly because bile acids reabsorbed due to the growth of the short circuits inside and outside the liver flow into the greater circulation, in addition to the substantial liver disorders. It is reported that the CA/CDCA ratio in liver cirrhosis is frequently smaller than 1 and the same tendency is observed in our study too. However the CA/CDCA ratios in many cases of not only liver cirrhosis but also acute hepatitis, chronic hepatitis and hepato cellular carcinoma fall within the standard level scope of healthy individuals without showing any difference. Also Abe et al. [refer to reference 8) in the above-mentioned list] report that the CA/CDCA ratios of fulminant hepatitis (FH) and liver cirrhosis are not significantly different from that of healthy individuals and that the CA+CDCA/DCA+UDCA ratio of FH is significantly higher than that of liver cirrhosis. According to the report of Abe et al., the reason therefor resides in the fact that the synthesis of the secondary bile acids is seriously inhibited in the case of FH due to an absolute increase in the primary bile acids and the inhibition of the discharge thereof into the bile, compared with the case of liver cirrhosis. As the result of the comparison of the CA+CDCA/DCA+UDCA ratios in our study, tendencies toward higher levels are observed in association with an increase in the severity (i.e., a higher ratio in liver cirrhosis than in chronic hepatitis, a higher ratio in hepato cellular carcinoma than in liver cirrhosis), though no clear significant difference is observed.

On the other hand, the means of the fraction data of a secondary bile acid DCA, among the serum bile acid components, show the closest approximations to each other regardless of the liver diseases, except the acute hepatitis cases of acute stage. The ratios of the primary bile acids (CA and CDCA) to this secondary bile acid DCA, i.e., CA/CDCA, CDCA/DCA and CA+CDCA/DCA are determined and the substantial differences in association with the liver disorders are discussed.

In the case of acute hepatitis, each fraction and TBA show abnormally high levels. The component ratios of nearly all of the cases fall within the standard level scope obtained from the healthy individuals. In particular, the dynamics of the serum bile acids in the acute stage of acute hepatitis are characterized in that each fraction and TBA show abnormally high levels but the component ratios fall within the standard level scope, similar to those of the convalescence stage of acute hepatitis.

In the case of chronic hepatitis, each fraction and TBA show abnormally high levels. Regarding the component ratios, however, the CA/DCA, CDCA/DCA and CA+CDCA/DCA ratios fall within the standard level scope in 7 cases among 13 (53.9%), while these ratios in 6 cases exceed the upper limits of the standard levels.

In liver cirrhosis, each fraction show an abnormally high level. Among all, the TBA value shows an extremely high level in association with a remarkable increase in CDCA. This is seemingly because in liver cirrhosis, CA is affected by the inhibition of 12α-hydroxylase but the synthesis of CDCA is scarcely affected thereby because of the existence of a side pathway [refer to reference 9) in the above-mentioned list]. The CDCA/DCA ratio (76.9%) shows the highest level exceeding the upper limit of the standard level, followed by the CA+CDCA/DCA ratio (53.9%) and the CA/DCA ratio (38.5%).

In hepato cellular carcinoma, all of the fractions show abnormally high levels except one case of DCA and TBA shows a similar tendency. Regarding the component ratios, the CDCA/DCA ratio show abnormally high levels exceeding the upper limit of the standard level in all cases (100%).

In particular, abnormally high levels of the CDCA/DCA ratio exceeding the standard levels clearly appear with an increase in the severity of chronic hepatitis, liver cirrhosis or hepato cellular carcinoma. It is therefore considered that this ratio reflects qualitative differences in the severity among liver diseases.

Also a similar tendency is observed in the CA+CDCA/DCA ratio, though it is so remarkable as in the case of the CDCA/DCA ratio.

On the basis of the above-mentioned findings, the method of the present invention, which comprises determining serum bile acid fractions and concentration ratios of bile acids (in particular, CDCA/DCA and CA+CDCA/DCA ratios) in order to diagnose a liver disease and to estimate the prognosis thereof, makes it possible to clarify the qualitative and quantitative changes in bile acids in detail compared with the conventional evaluation method depending exclusively upon the total bile acid concentration. Since the liver has a large capacity of compensation and reservation, it is highly important from a clinical viewpoint to certainly diagnose the severity of a clinical disease. Therefore it is highly useful in clinical medicine to employ the method of the present invention as an indication for evaluating the severity of a liver disease. Hopefully, the accumulation of clinical data will contribute to the application of the method of the present invention to more accurate and detailed diagnoses.

Literature list

1) Kano M., Wada H., Matsumoto M., Yamamoto K., Kamano T., Motegi K., Oguchi K. and Kano Y.: Human fecal bile acids and fractions with enzyme-linked immunosorbent assay, Showa Univ. J. Med. Sci., 5: 183–191 (1993)

2) Reddy B. S. and Wynder E. L.: Metabolic epidemiology of colon cancer, Fecal bile acid and neutral sterols in colon cancer patients and patients with adenomatous polyps, Cancer, 39:2533–2539 (1977)

3) Kumada T., Nakano S., Ohta H., Sasaki T., Kitamura K., Watahiki H., Takeda I., Okuyama S. and Takagi K.; Clinical evaluation on determination of individual bile acids in liver diseases, serum bile acid composition in fulminant hepatitis and acute hepatitis, Kanzhs, 23: 364–371 (1982) (in Japanese, English abstract)

4) Karlaganis G. and Paumgartner G.: Determination of bile acids in serum by capillary gas-liquid chromatography, Clin. Chim. Acta, 92: 19–26 (1979)

5) Maruyama K., Tanimura H. and Hikasa Y.: Analysis of conjugated bile acids in bile by high pressure liquid chromatography, Clin. Chim. Acta, 100: 47–54 (1980)

6) Mashige F., Tanaka N., Maki A., Kamei S. and Yamanaka M.: Direct spectrophotometry of total bile acids in serum, Clinchem., 27: 1352–1356 (1981)

7) Inaguma H., Katagiri K., Tsukada K., Hirose A., Hoshino M., Hayakawa T., Yokochi M., Miyaji M., Ito M. and Takeuchi T.: Serum bile acid composition in fulminant hepatitis, comparative study with acute hepatitis, Nagoya Med. J., 29: 63–71 (1984)

8) Abe K., Yoshiba M. and Sugata F.: Clinical significance of kinetics of serum bile acid fractions in patients with fulminant hepatitis and liver cirrhosis, J. Showa Med. Assoc., 53: 25–30 (1993) (in Japanese, English abstract)

9) Ayaki Y. and Yamasaki K.: In vitro conversion of 7α-hydroxycholesterol to some natural $C_{24}$-bile acids with special reference to chenodeoxycholic acid biogenesis, J. Biochem., 68: 341–346 (1970).

What is claimed is:

1. A method for diagnosing the presence of a liver disease in an individual to be tested comprising:
   (a) individually measuring the concentration of each bile acid in the group consisting of cholic acid, chenodeoxycholic acid, deoxycholic acid and ursocholic acid in a serum sample from the individual to be tested, according to the following steps:
   for each of the bile acids,
     (i) preparing an ester of the bile acid;
     (ii) reacting a portion of the ester with bovine serum albumin to produce an immunogen, dialyzing the immunogen, immunizing a mammal other than a human being with the dialyzed immunogen to obtain an anti-bile acid antibody;
     (iii) reacting another portion of the ester with an enzyme to produce an enzyme-labelled bile acid;
     (iv) providing a microtiter plate, wherein each well is coated with an anti-species immunoglobulin antibody, wherein the species is the same species as that of the immunized mammal;
     (v) contacting individual wells of the microtiter plate with (A) the anti-bile acid antibody, (B) the enzyme-labelled bile acid, and (C) either an aliquot of the serum sample from the individual being tested, a serum sample from a healthy individual or a control sample comprising a known concentration of the bile acid;
     (vi) washing the microtiter plate of step (e);
     (vii) contacting the individual wells of the microtiter plate with a substrate for the labelling enzyme to produce a detectable product in proportion to the amount of bound enzyme-labeled bile acid in the individual well;
     (viii) measuring the absorbance of the individual wells;
     (ix) constructing a standard curve based upon the absorbance of the control sample; and,
     (x) determining the concentrations of the serum bile acid in the serum sample from the individual being tested and from the healthy individual using the standard curve;

(b) calculating total bile acid concentrations for both the individual being tested and the healthy individual;

(c) calculating an individual bile acid/total bile acid concentration ratio for each bile acid for both the individual being tested and the healthy individual; and, (d) comparing corresponding bile acid ratios between the individual being tested and the healthy individual wherein an increased bile acid ratio in the individual being tested indicates the presence of liver disease.

2. The method as claimed in claim 1 wherein said enzyme is horseradish peroxidase, said substrate is a o-phenylenediamine and said mammal to be immunized is rabbit.

3. The method as claimed in claim 2 wherein the absorbance is measured at 492 nm.

4. The method as claimed in claim 1, wherein based upon (i) said calculated individual bile acid/total bile acid concentration ratio of each of said bile acids for both the individual being tested and the healthy individual and (ii) said comparison of corresponding bile acid ratios between the individual being tested and the healthy individual, an increase in one or more bile acid ratios in the individual being tested determines said liver disease to be one selected from the group consisting of acute hepatitis, chronic hepatitis, liver cirrhosis or hepato cellular carcinoma.

5. A method for diagnosing the presence of a liver disease in an individual to be tested comprising:

(a) individually measuring the concentration of each bile acid in the group consisting of cholic acid, chenodeoxycholic acid, deoxycholic acid and ursocholic acid in a serum sample from the individual to be tested, according to the following steps:

for each of the bile acids, (i) preparing an ester of the bile acid;

(ii) reacting a portion of the ester with bovine serum albumin to produce an immunogen, dialyzing the immunogen, immunizing a mammal other than a human being with the dialyzed immunogen to obtain an anti-bile acid antibody;

(iii) reacting another portion of the ester with an enzyme to produce an enzyme-labelled bile acid;

(iv) providing a microtiter plate, wherein each well is coated with an anti-species immunoglobulin antibody, wherein the species is the same species as that of the immunized mammal;

(v) contacting individual wells of the microtiter plate with (A) the anti-bile acid antibody, (B) the enzyme-labelled bile acid, and (C) either an aliquot of the serum sample from the individual being tested, a serum sample from a healthy individual or a control sample comprising a known concentration of the bile acid;

(vi) washing the microtiter plate of step (e);

(vii) contacting the individual wells of the microtiter plate with a substrate for the labelling enzyme to produce a detectable product in proportion to the amount of bound enzyme-labeled bile acid in the individual well;

(viii) measuring the absorbance of the individual wells;

(ix) constructing a standard curve based upon the absorbance of the control sample; and, (x) determining the concentrations of the serum bile acid in the serum sample from the individual being tested and from the healthy individual using the standard curve;

(b) calculating an individual cholic acid/deoxycholic acid concentration ratio and chenodeoxycholic acid/deoxycholic acid concentration ratio for both the individual being tested and the healthy individual; and (c) comparing corresponding bile acid concentration ratios between the individual being tested and the healthy individual wherein an increased bile acid ratio in the individual being tested indicates the presence of liver disease.

6. A method for diagnosing the presence of a liver disease in an individual to be tested comprising:

(a) individually measuring the concentration of each bile acid in the group consisting of cholic acid, chenodeoxycholic acid, deoxycholic acid and ursocholic acid in a serum sample from the individual to be tested, according to the following steps:

for each of the bile acids, (i) preparing an ester of the bile acid;

(ii) reacting a portion of the ester with bovine serum albumin to produce an immunogen, dialyzing the immunogen, immunizing a mammal other than a human being with the dialyzed immunogen to obtain an anti-bile acid antibody;

(iii) reacting another portion of the ester with an enzyme to produce an enzyme-labelled bile acid;

(iv) providing a microtiter plate, wherein each well is coated with an anti-species immunoglobulin antibody, wherein the species is the same species as that of the immunized mammal;

(v) contacting individual wells of the microtiter plate with (A) the anti-bile acid antibody, (B) the enzyme-labelled bile acid, and (C) either an aliquot of the serum sample from the individual being tested, a serum sample from a healthy individual or a control sample comprising a known concentration of the bile acid;

(vi) washing the microtiter plate of step (e);

(vii) contacting the individual wells of the microtiter plate with a substrate for the labelling enzyme to produce a detectable product in proportion to the amount of bound enzyme-labeled bile acid in the individual well;

(viii) measuring the absorbance of the individual wells;

(ix) constructing a standard curve based upon the absorbance of the control sample; and, (x) determining the concentrations of the serum bile acid in the serum sample from the individual being tested and from the healthy individual using the standard curve;

(b) calculating an individual (cholic acid+chenodeoxycholic acid)/deoxycholic acid concentration ratio and chenodeoxycholic acid/deoxycholic acid concentration ratio for both the individual being tested and the healthy individual; and (c) comparing corresponding bile acid concentration ratios between the individual being tested and the healthy individual wherein an increased bile acid ratio in the individual being tested indicates the presence of liver disease.

* * * * *